United States Patent [19]
Leiner et al.

[11] Patent Number: 6,124,135
[45] Date of Patent: Sep. 26, 2000

[54] METHOD OF DETERMINING AN ALKALI ION

[75] Inventors: Marco Jean Pierre Leiner, Graz, Austria; Huarui He, Alpharetta, Ga.; Andrei Boila-Göckel, Graz, Austria

[73] Assignee: AVL Medical Instruments, Schaffhausen, Switzerland

[21] Appl. No.: 09/085,807

[22] Filed: May 27, 1998

[30] Foreign Application Priority Data

May 30, 1997 [AT] Austria ...................................... 930/97

[51] Int. Cl.[7] .................................................. G01N 33/20
[52] U.S. Cl. .............................. 436/79; 436/73; 436/74; 436/172; 422/82.06
[58] Field of Search .................... 540/469; 422/82.05, 422/82.06, 82.07, 82.08; 436/73, 79, 172, 74

[56] References Cited

U.S. PATENT DOCUMENTS

| | | | |
|---|---|---|---|
| 4,774,339 | 9/1988 | Haugland et al. | 548/405 |
| 4,843,158 | 6/1989 | Smith | 540/469 |
| 5,162,525 | 11/1992 | Masilamani et al. | 540/468 |
| 5,439,828 | 8/1995 | Masilamani et al. | 436/74 |
| 5,474,743 | 12/1995 | Trend et al. | 422/82.07 |
| 5,516,911 | 5/1996 | London et al. | 548/236 |

OTHER PUBLICATIONS

O.A. Gansow et al. *J. Heterocycl. Chem*, 1981, 18, 297–302.
B.G. Cox et al. *Ber. Bunsenges. Phys. Chem.* 1982, 86, 293–297.
O.A. Gansow et al. *Inorg. Chim. Acta* 1985, 109, 1–6.
R.A. Bartsch et al. *J. Inclusion Phenom. Mol. Recognit. Chem.* 1990, 9, 113–123.
O.J. Jung *Bull. Korean Chem. Soc.* 1993, 14, 687–691.
F. Kastenholz et al. *J. Fluoresc.* 1994, 4, 243–246.
B. Gersch et al. *Tetrahedron Lett.* 1996, 37, 2213–2216.
D.A. Dantz et al. *Polyhedron* 1998, 17, 1891–1895.

(List continued on next page.)

CA 99:177723h.

*Primary Examiner*—Arlen Soderquist
*Attorney, Agent, or Firm*—Baker Botts LLP

[57] ABSTRACT

The invention relates to a method of determining an alkali ion in a sample, wherein the alkali ion is contacted with a compound having a luminophoric moiety and an ionophoric moiety, which ionophoric moiety reacts with the alkali ion present in the sample, wherein the luminophoric moiety changes its luminescence properties, after which the luminescence is measured and the alkali ion determined utilizing the test reading, which method is characterized in that the compound utilized is a diaza-cryptand of the general Formula I:

(I)

$$X-(CH_2)_m-\text{[diaza-cryptand structure]}$$

in which X is the luminophoric moiety, m is the number 0, 1 or 2, and o and p independently mean the numbers 0, 1 or 2.

4 Claims, 5 Drawing Sheets

OTHER PUBLICATIONS

J.R. Lakowicz, "Topics in Fluorescence Spectroscopy", vol. 4: Probe Design and Chemical Sensing, pp. 133–134 (Plenum Press, New York and London) (1994).

Frank Kastenholz, Inaugural Dissertation, University of Cologne, Fig. 32, p. 54 (1993).

R. Crossley, Zia Goolamali and Peter G. Sammes, "Synthesis and Properties of a Potential Extracellular Fluorescent Probe for Potassium", J. Chem. Soc. Perkin Trans. 2, pp. 1615–1622 (1994).

M.J.P. Leiner, P. Hartmann, "Theory and practice in optical pH sensing", Sensors and Actuators B, vol. 11, pp. 281–289 (1993).

A.P. de Silva, et al., Tetrahedron Letters, "A New Benzo–Annelated Cryptand and a Derivative with Alkali Cation–Sensitive Fluorescence", vol. 31, No. 36, pp. 5193–5196 (1990).

B. Dietrich, J.M. Lehn, J.P. Sauvage, J. Blanzart, "Syntheses et Proprietes Physiques De Systemes Diaza–Polyoxa–Macrobicycliques", Tetrahedron vol. 29, pp. 1629–1645 (1973).

METHOD OF DETERMINING AN ALKALI ION

The present invention relates to a method of determining an alkali ion in a sample, wherein the alkali ion is contacted with a compound (=luminophore-ionophore) having a luminophoric moiety and an ionophoric moiety, which ionophoric moiety reacts with the alkali ion present in the sample, wherein the luminophoric moiety changes its luminescence properties, after which the luminescence is measured and the concentration or the activity of the alkali ion are deduced, i.e. the alkali ion is determined, utilizing the test reading. The invention also relates to diaza-cryptands capable of being used as luminophore-ionophores for determining an alkali ion.

BACKGROUND OF THE INVENTION

A determination method of this type is based on the so-called "PET effect". This latter term denotes the transfer, induced by photons, of electrons (photoinduced electron transfer =PET) from the ionophoric moiety or ionophore, respectively, to the luminophoric moiety or luminophore, respectively, which leads to a decrease in the (relative) luminescence intensity and the luminescence decay time of the luminophore. Absorption and emission wavelengths, however, remain basically unaffected in the process (J. R. Lakowicz in "Topics in Fluorescence Spectroscopy", Volume 4: Probe Design and Chemical Sensing; Plenum Press, New York & London (1994)).

By the binding of ions to the ionophore, the PET effect is partly or completely inhibited, so that there is an increase in the luminescence of the luminophoric moiety. Hence, the concentration or the activity of the ion to be determined can be deduced by measuring the change in luminescence properties, i.e. luminescence intensity and/or luminescence decay time.

From U.S. Pat. No. 5,516,911, fluorescence indicators for determining intracellular calcium are known which carry fluorescent substituents capable of acting as optical indicators.

A method of the kind initially described is known from U.S. Pat. No. 5,439,828, wherein diaza-cryptands are utilized as the luminophore-ionophore, which diaza-cryptands have been functionalized as fluorophores with fluorescent coumarins and, depending on their structure, are selective for lithium, sodium and potassium ions, respectively. It is stated that these luminophore-ionophores can be used in sample media of neutral pH and are even the preferred choice in such systems.

Yet, research (Frank Kastenholz, Inaugural Dissertation, University of Cologne, 1993, FIG. 32, p. 54) has shown that in the physiological pH range the fluorescence signal depends significantly on the pH of the sample and increases considerably with decreasing pH, even from pH 7.4 onwards. This affects the accuracy of a determination carried out in a biological sample. Moreover, the compounds that are being used have the added disadvantage that the employed coumarins show absorption wavelengths of about 336 nm and hence cannot be excited by commercial LEDs.

DETAILED DESCRIPTION OF THE PREFERRED EMBODIMENTS

Figure 1:
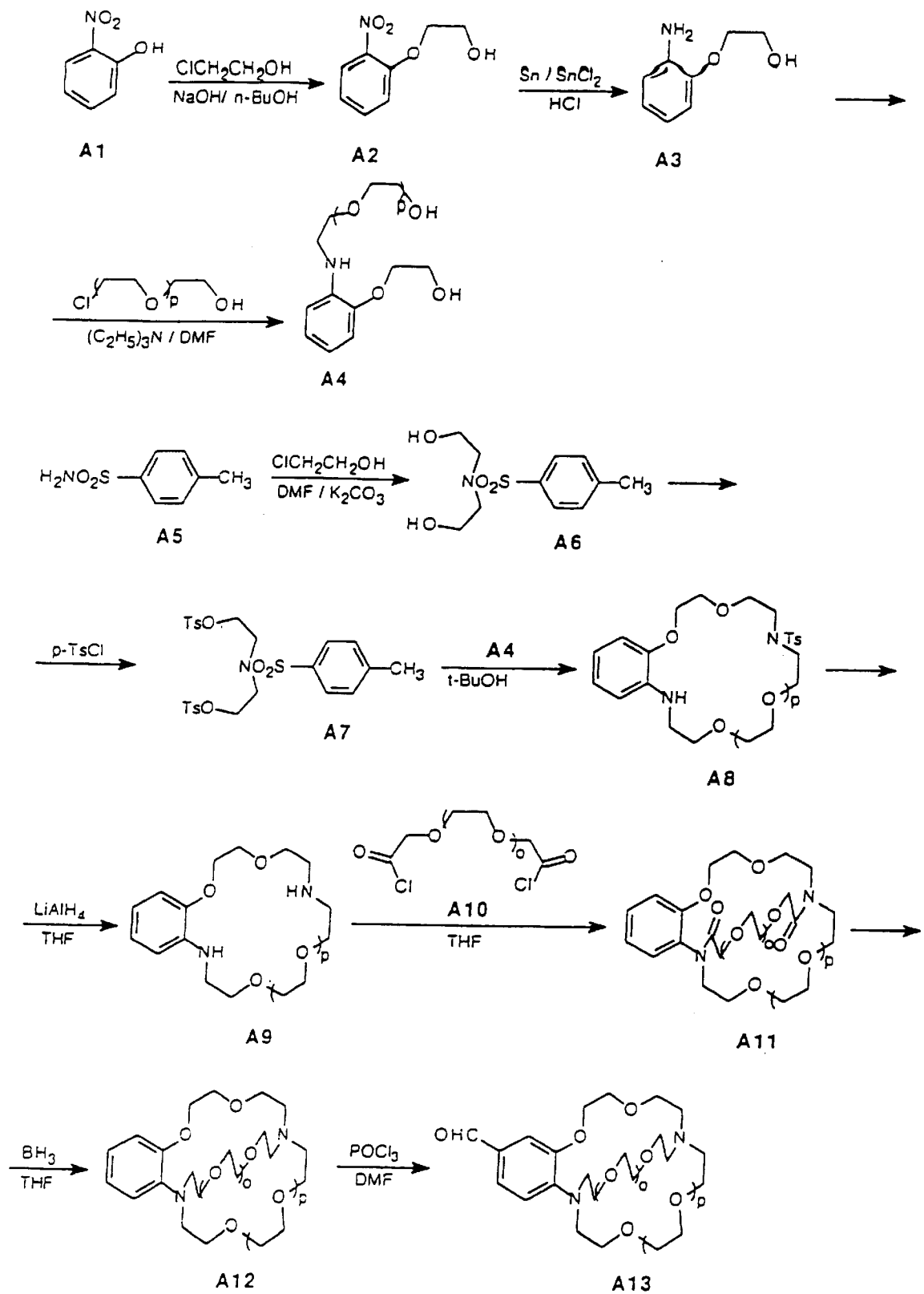
FIG. 1 is an illustration of a synthetic pathway for an ionophoric moiety of a diaza-cryptand in accordance with the invention.

These disadvantages also apply to the luminophore-ionophores mentioned in U.S. Pat. No. 5,162,525.

From Tetrahedron Letters, Volume 31, No. 36, pp. 5193–5196 (1990), diaza-cryptands are known in which the two nitrogen atoms are bound to a respective aromatic ring each, i.e. are aryl nitrogens and aniline-type nitrogens, respectively. Research conducted by the applicant has shown that these diaza-cryptands are not suited for determining potassium ions if they are present in the physiological range of concentration and at physiological pH values of the blood (7.0–7.6).

SUMMARY OF THE INVENTION

The present invention therefore has as its object to improve the known process or make available luminophore-ionophores which lack significant dependence of the luminescence properties on the pH value of the sample at physiological pH values and thus are suited for determination in biological samples.

Further, the method of the invention is to be particularly well suited for practice in the presence of physiological concentrations of alkali ions, i.e. it should exhibit a strong dependence of the luminescent signal on the concentration of the alkali ion being determined.

In the method initially described, this object is achieved in that the compound (=luminophore-ionophore) utilized is a diaza-cryptand of the general Formula I:

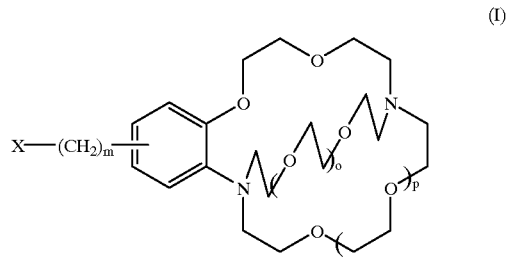

(I)

in which X is the luminophoric moiety, m is the number 0, 1 or 2, and o and p independently mean the numbers 0, 1 or 2.

The diaza-cryptands showing the above general Formula I are novel. These novel luminophore-ionophores have been found to be very useful for determining alkali ions at physiological pH values and at physiological concentrations.

The diaza-cryptands of the invention of the general Formula I have been found to be particularly useful for determining lithium ions in the concentration range between 0.30 and 2.1 mmol/l and potassium ions in the concentration range between 1.5 and 8.0 mmol/l.

Without being bound to a specific theory, it is assumed that the advantageous properties of the diaza-cryptands of the invention are due to the fact that in the ionophoric moiety one of the nitrogens is an aryl nitrogen and the other nitrogen is an aliphatic nitrogen.

Suitable luminophoric moieties X would be all those moieties by which in combination with the ionophoric moiety a PET effect can be achieved. A great number of moieties is known from literature which in combination with the ionophore give a PET effect or in principle are suited for this purpose. By coupling these known moieties to the benzene ring of the general Formula I, new compounds are obtained which may be examined by the man skilled in the art in order to find out whether a PET effect can be obtained. Coupling may be in a position ortho to the nitrogen, in its two meta positions and in para position. The para position is the preferred position.

Those skilled in the art will be aware that in order for a PET effect to materialize it is essential in particular that the electron donor of the ionophoric moiety be electronically decoupled from the electronic system of the luminophoric moiety. As is well known in the art, such electronic decoupling of the ionophoric and luminophoric moieties may be achieved in that the two moieties present are separated either by a spacer group, i.e. the $(CH_2)_m$ chain with $m>0$ or—if $m=0$—by a virtual spacer (f.i. by pivoting the plane of the luminophoric moiety to the plane of the benzene ring). Hence, the function of the spacer is to oppose conjugation of the electron system of the ionophoric moiety with the electron system of the luminophoric moiety.

Electronic decoupling can be recognized fi. from the fact that there is no significant change concerning the wavelengths of the absorption and emission spectra.

For determining lithium ions, a diaza-cryptand of the general Formula I is preferably utilized in which o and p mean the numbers 0 and 0, respectively.

For determining sodium ions there is preferably utilized a diaza-cryptand of the general Formula I in which o and p mean the numbers 0 and 1, respectively, or the numbers 1 and 0, respectively.

For determining potassium ions, a diaza-cryptand of the general Formula I is preferably utilized in which o and p mean the numbers 1 and 1, respectively.

The luminophoric moiety X in the general Formula I preferably is an amino-naphthalimide group of the general Formula II

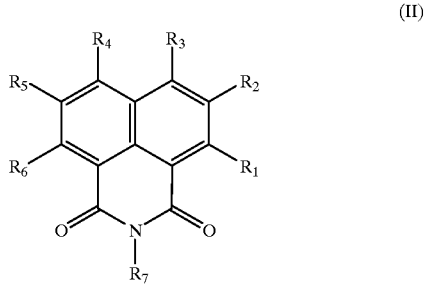

(II)

in which one of $R_1$, $R_2$, $R_3$, R4, $R_5$ and R6 is a group —NH— through which X is bound to the group —$(CH_2)_m$—of the above-recited compound of the general Formula I and the remainder and $R_7$ each independently are hydrogen, a lipophilic or hydrophilic group or a reactive group for coupling to a polymer, or is a xanthenone group of the general Formula III

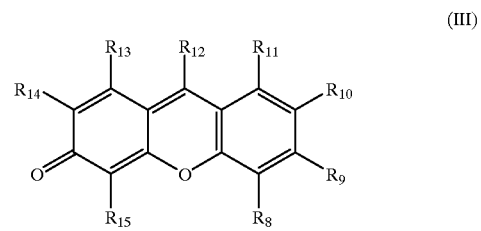

(III)

in which one of $R_8$, $R_9$, $R_{10}$, $R_{11}$, $R_{12}$, $R_{13}$, $R_{14}$ and $R_{15}$ represents a chemical bond through which X is bound directly (m=0) to the ionophoric moiety of the above-recited compound of the general Formula I and the remainder represent —OH, —$OR_{16}$, in which $R_{16}$ is a hydrophilic or a lipophilic group, —O—$R_{17}$—G, in which $R_{17}$ is a hydrophilic or a lipophilic group and G a reactive group for coupling to a polymer, or —$(CH_2)_n$—COOH, in which n is a number between 0 and 17.

It is preferred that in the general Formula II $R_3$ or R4 be the group —NH— through which the luminophoric moiety is bound to the group —$(CH_2)_m$—of the above-mentioned general Formula I.

It is further preferred that in the general Formula III $R_{12}$ be a chemical bond through which the luminophoric moiety is bound directly (m=0) to the ionophoric moiety of the above-mentioned general Formula I.

Suitable lipophilic groups would f.i. be substituted and unsubstituted alkyl groups and alkoxy groups having up to 20 C atoms.

Suitable hydrophilic groups would f.i. be alkyl groups having 1–17 C atoms and carrying at least one hydroxyl group and/or functional groups which at the pH of the measuring solution are present in a dissociated condition, such as f.i. carboxylic acids, sulfonic acids and phosphoric acids.

Reactive groups for coupling to aminofunctionalized polymers, f.i. aminocellulose and aminofunctional polyacrylamides, are known f.i. from U.S. Pat. No. 4,774,339, Table 4.

These above-recited luminophoric moieties, which are preferably utilized, may be excited using light of a wavelength of >450 nm.

The compounds of the invention for determining the alkali ions may be added to the sample solution in dissolved condition. However, they may also be components of a sensor, where they may be embedded in a layer formed f.i. from a hydrogel, as will be described hereinbelow with reference to FIG. 2.

The invention further relates to a diaza-cryptand of the general Formula IV:

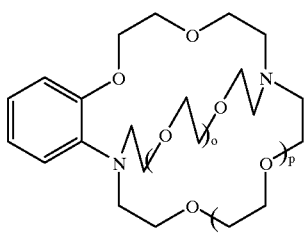

(IV)

in which o and p independently mean the numbers 0, 1 or 2. This cryptand forms the ionophoric moiety of the compounds of the invention of the general Formula I.

In the following, the invention will be described in more detail by means of examples, wherein the synthesis and properties of some diaza-cryptands which are preferably used will be explained. Other compounds in accordance with the invention can be prepared in analogous manner by the person skilled in the art.

1. Synthesis of the Diaza-cryptands of the Invention

1.1. Synthesis of the Ionophoric Moiety of the Diaza-cryptands of the Invention (FIG. 1)

General Process (FIG. 1)

The synthetic pathway for the ionophoric moiety of the diaza-cryptands of the invention is represented generally in FIG. 1

2-nitrophenol A1 was reacted with 2-chloroethanol in n-butanol and sodium hydroxide to give 2'-(2'-hydroxyethoxy)nitrobenzene A2. By reducing this compound with Sn/SnCl$_2$/HCl, the 2-(2-hydroxyethoxy)aniline A3 was obtained which then with 2-chloroethanol and with 2-(2-chloroethoxy)ethanol, respectively, in dimethylformamide in the presence of triethylamine yielded the N-alkylated aniline derivatives A4 with p=0 and p=1, respectively. By warming 4-toluenesulfonamide A5 with 2-chloroethanol in dimethylformamide and potassium carbonate, the N,N-bis(2-hydroxyethyl)-4-toluenesulfonamide A6 was obtained which then with 4-toluenesulfonic acid chloride yielded the corresponding ditosylate A7.

The ditosylate A7 was then reacted with the N-alkylated aniline derivatives A4 with p=0 and p=1, respectively, in t-butanol/tetrahydrofuran and potassium-t-butoxide as the base to give the corresponding diaza-crown ether toluenesulfonamides A8 with p=0 and p=1, respectively. The pure products were obtained through column chromatography on silica gel. Splitting off of the tosyl group was with lithium aluminum hydride in tetrahydrofuran under reflux, wherein the diaza-crown ethers A9 with p=0 and p=1, respectively, were obtained. 3-oxapentane-dicarboxylic acid dichloride A10 with o=0 and 3,6-dioxaoctanedicarboxylic acid dichloride A10 with o=1 were obtained from the corresponding dicarboxylic acids with oxalic acid dichloride in benzene. The cryptand-bis-amides A11 with o=0, p=0 and o=0, p=1, respectively, were prepared under heavy dilution from the diaza-crown ethers A9 with p=0 and p=1, respectively, by reaction with 3-oxapentane dicarboxylic acid dichloride A10 with o=0 in tetrahydrofuran. The cryptand-bis-amides A11 with o=l, p=0 and o=1p=1, respectively, were obtained in analogous manner from the diaza-crown ethers A9 with p=0 and p=1, respectively, with 3,6-diazaoctane-dicarboxylic acid dichloride A10 with o=1. Reduction of the amide groups with borane-tetrahydrofuran complex in tetrahydrofuran yielded the diaza-cryptands A12 with o=0, p=0 and o=0, p=1, respectively. and o=1, p=0 and o=1, p=1, respectively.

Introduction of the aldehyde function was through direct formylation with phosphorus oxytrichloride in dimethylformamide, wherein the corresponding diaza-cryptand-aldehydes A13 with o=0, p=0 and o=0, p=1, respectively, and o=1, p=0 and o=1, p=1, respectively, were obtained.

In analogous manner it is feasible to obtain compounds A13 in which o and p independently also mean the number 2.

Figure 2:
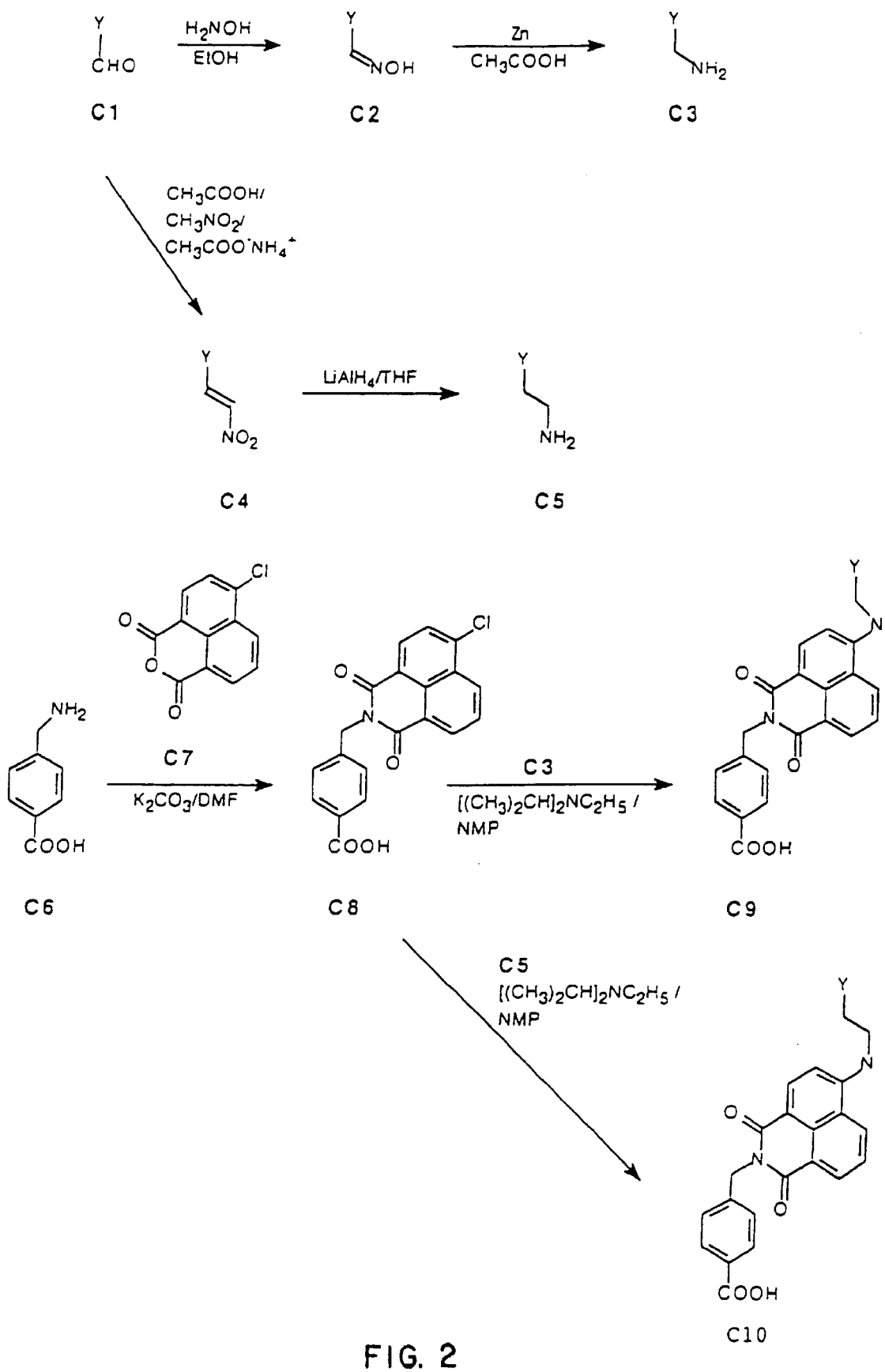
FIG. 2 is an illustration of a synthetic pathway of a luminophoric moiety which is an amino-naphthalimide group, in accordance with the invention.

Description of Individual Reaction Steps of FIG. 1
2-(2-hydroxyethoxy)nitrobenzene A2:

10 g (71.88 mmol) 2-nitrophenol A1 and 3.59 g (89.86 mmol) sodium hydroxide were dissolved in 55 ml n-butanol and 5 ml water at 70° C., 6.26 ml (7.52 g, 93.44 mmol) 2-chloroethanol were slowly added drop by drop. This was followed by three days of vigorous stirring at 100° C. After cooling, the reaction mixture was filtrated, the precipitate washed with chloroform and the filtrate reduced. The residue was taken up in chloroform and washed three times with aqueous 10% sodium hydroxide solution. Then the organic phase was dried over sodium sulfate and was concentrated in vacuo. 10.8 g of bright yellow crystals were obtained; yield 82%.

$^1$H NMR (CDCl$_3$), δ (ppm): 3.97 (m, 3H), 4.22 (t, 2H), 6.98–7.13 (m, 2H), 7.52 (m, 1H), 7.83 m, 1H).
2-(2-hydroxyethoxy)aniline A3:

8.9 g (48.59 mmol) 2-(2-hydroxyethoxy)nitrobenzene A2, 16.44 g (72.88 mmol) SnCl$_2$. 2H$_2$O and 17.3 g (145.77 mmol) tin were stirred in 30.84 ml aqueous HCl (30%) and 25 ml water at 90° C. for 8 hours. After cooling, the solution was treated with aqueous 5n sodium hydroxide solution and stirred for 3 hours at 90° C. The aqueous solution was subsequently decanted, wherein, upon cooling, the crude product crystallized out and was removed by suction. This crude product was then taken up in methanol, warmed and the suspension was filtered. The filtrate was then concentrated in vacuo. 6 g of light-brown crystals were obtained; yield 80%.

$^1$H NMR (CDCl$_3$), δ (ppm): 3.62 (m, 3H), 3.97 (t, 2H), 6.52–6.75 (m, 4H).
N-[2-(2-hydroxyethoxy)ethyl]-2-(2-hydroxyethoxy)aniline A4 (p=1):

6 g (39.17 mmol) 2-(2-hydroxyethoxy)aniline A3, 5 ml (5.85 g, 47 mmol) 2-(2-chloroethoxy)ethanol and 8.19 ml (5.95 g, 58.75 mmol) triethylamine were dissolved in 20 ml dimethylformamide and stirred for 4 days at 90° C. After cooling, the solution was filtered, the precipitate washed with dichloromethane and the filtrate concentrated in vacuo. The residue was taken up in chloroform and washed twice with a small quantity of water. The chloroform solution was then dried over sodium sulfate and concentrated. The viscous crude product was purified by column chromatography on silica gel 60 with toluene/acetone 1:2 as the mobile phase. 5 g of brown, viscous oil were obtained; yield 53%.

$^1$H NMR (CDCL$_3$), δ (ppm): 3.26 (m, 2H), 3.52 (m, 2H), 3.67 (m, 4H), 3.83 (m, 2H), 4.00 (m, 2H), 4.56 (br s, 2H), 6.55–6.95 (m, 4H).
N,N-bis(2-hydroxyethyl)-4-toluenesulfonamide A6:

6.84 g (40 mmol) 4-toluenesulfonamide A5, 7 ml (8.37 g, 104 mmol) 2-chloroethanol and 27.64 g (200 mmol) potassium carbonate were suspended in 100 ml dimethylformamide and stirred for 3 days at 110° C. Upon cooling, the reaction mixture was filtrated and the precipitate washed with chloroform. The filtrate was concentrated, the oily residue taken up in chloroform and finally washed with a 10% sodium hydroxide solution. On concentrating the organic solution, 8.4 g of pure product were obtained as light yellow crystals; yield: 81%.

$^1$H NMR (CDCL$_3$), δ (ppm) : 2.39 (s, 3H), 3.21 (t, 4H), 3.82 (t, 4H), 4.50 (br s, 2H), 7.29 (d, 2H), 7.65 (d, 2H).
N,N-bis(2-hydroxyethyl)-4-toluenesulfonamide-bis-toluenesulfonate A7:

4.54 g (17.5 mmol) N,N-bis(2-hydroxyethyl)-4-toluenesulfonamide A6 were dissolved in 20 ml acetone and cooled down to −5° C. Then, 8 g (42 mmol) 4-toluenesulfonic acid chloride were added, followed by stirring for 10 min. An aqueous 25% sodium hydroxide solution was slowly added drop by drop at -2° C., then stirring was continued for 8 hours at 0° C. and the reaction mixture placed in a refrigerator overnight. The mixture was poured onto ice-water, with the product precipitating as a viscous oil. The aqueous phase was carefully decanted, the product taken up in chloroform and washed with water. On concentration of the solvent, 9.2 g of pure product were obtained as a light yellow viscous oil which slowly crystallized in the cold; yield: 92%.

$^1$H NMR (CDCL$_3$), δ (ppm): 2.41 (s, 3H), 2.46 (s, 3H), 3.36 (t, 4H), 4.10 (t, 4H), 4.50 (br s, 2H), 7.29 (d, 2H), 7.34 (d, 4H), 7.62 (d, 2H), 7.76 (d, 4H).
Diaza-crown ether toluenesulfonamide A8 (p=1):

5 g (20.72 mmol) aniline derivative A4 (p=1) and 6.05 g (53.88 mmol) potassium-t-butoxide were dissolved in 280 ml t-butanol under a nitrogen atmosphere and stirred for 2 hours at 60° C. Then, 11.76 g (20.72 mmol) toluenesulfonate A7 in 140 ml dry tetrahyrofuran were added dropwise over a period of 2 h at 40° C. The reaction mixture was subsequently stirred for 48 hours at 60° C. After cooling, the solution was filtered, the precipitate washed with dichloromethane and the filtrate concentrated in vacuo. The residue was dissolved in chloroform and washed with water twice. Finally the organic solution was concentrated, with a dark oily residue forming. From the latter, the product was obtained through column chromatography on silica gel, using toluene/acetone 10:9 as the mobile phase: 1 g of yellow, viscous oil; yield: 10%.

$^1$H NMR (CDCL$_3$), δ (ppm): 2.40 (s, 3H), 3.20–4.50 (m, 20H), 6.55–6.96 (m, 4H), 7.27 (d, 2H), 7.67 (d, 2H).
Diaza-crown ether A9 (p=1):

0.41 g (10.8 mmol) lithium aluminum hydride were suspended in 10 ml dry tetrahydrofuran under a nitrogen atmosphere and 0.5 g (1.08 mmol) diaza-crown ether toluenesulfonamide A8 (p=1) in 10 ml tetrahydrofuran were slowly added drop by drop. The reaction mixture was stirred under reflux for 3 days. After cooling, excess lithium aluminum hydride was decomposed using tetrahydrofuran/water 2:1 (v/v), filtered and the precipitate washed with dichloromethane. The residue was taken up in dichloromethane, filtered and the solvent removed in vacuo. 0.25 g of light-brown oil were obtained; yield: 75%.
Cryptand-bis-amide A11 (o=1, p=1):

This reaction was carried out according to the method of R. Crossley, Z. Goolamali, P. G. Sammes, J. Chem. Soc. Perkin Trans. 2, 1994, 1615–1622. The dicarboxylic acid dichloride A10 (o=0) was obtained by the method of B. Dietrich, J. M. Lehn, J. P. Sauvage, J. Blanzat, Tetrahedron 1973, 29, 1629–1645.

A solution of 0.13 g (1.67 mmol) pyridine in 240 ml dry tetrahydrofuran was prepared and cooled down to 0° C. Subsequently, 0.25 g (0.805 mmol) diaza-crown ether A9 (p=1) in 40 ml dry tetrahydrofuran and 0.17 g (0.605 mmol) 3,6-dioxaoctane dicarboxylic acid dichloride A10 (o=1) in 40 ml dry tetrahydrofuran were added simultaneously in dropwise manner over a period of 4 hours. The reaction mixture was then stirred for another 40 hours at 0° C. The mixture was filtered and the tetrahydrofuran removed. The oily, brown residue was dissolved in chloroform, washed with diluted HCl and then with water. The chloroform solution was dried over sodium sulfate and concentrated. An oily, light-brown residue was obtained; yield: 0.12 g (33%).
Diaza-cryptand A12 (o=1, p=1):

0.12 g (0.27 mmol) cryptand-bis-amide A11 (o=1, p=1) were placed in a three-necked flask provided with a nitrogen supply, a septum and a reflux cooler with calcium-chloride tubes. 2.5 ml dry tetrahydrofuran were added through the septum by means of a syringe and the suspension was cooled in an ice bath. Then, 2.2 ml (2.2 mmol) of 1 m borane-THF-complex solution were added cautiously, also through the septum. After 10 min, the ice bath was removed, the reaction mixture was stirred at room temperature for 30 min and subsequently under reflux for 2 hours. After cooling, the mixture was cautiously mixed with 1 ml water and 10 ml aqueous 6 n HCl and stirred for 1 hour at room temperature. The solvent was removed in vacuo and the resulting white suspension adjusted to pH 10 with an aqueous lithium hydroxide solution. The aqueous phase was extracted with chloroform. On concentrating the solution in vacuo, a light-brown oil was obtained; yield: 0.1 g (88%).
Diaza-cryptand-aldehyde A13 (o=1, p=1):

A solution of 0.5 g (1.18 mmol) diaza-cryptand A12 (o=1, p=1) in 1.5 ml dimethylformamide was prepared and cooled to −10° C. 0.22 ml (0.36 g, 2.35 mmol) phosphorus oxytrichloride were added cautiously drop by drop so that the temperature did not exceed 0° C. The reaction mixture was stirred for 15 min at −5° C., then at room temperature overnight and, finally, for hour at 60° C. After cooling, the mixture was mixed with water, adjusted to pH 9 with an aqueous concentrated lithium hydroxide solution and was stirred for 30 min. The solution was extracted 3 times using 30 ml chloroform in each case and the organic phase was concentrated in vacuo. 0.32 g of yellow oil were obtained; yield: 60%.

Figure 3:
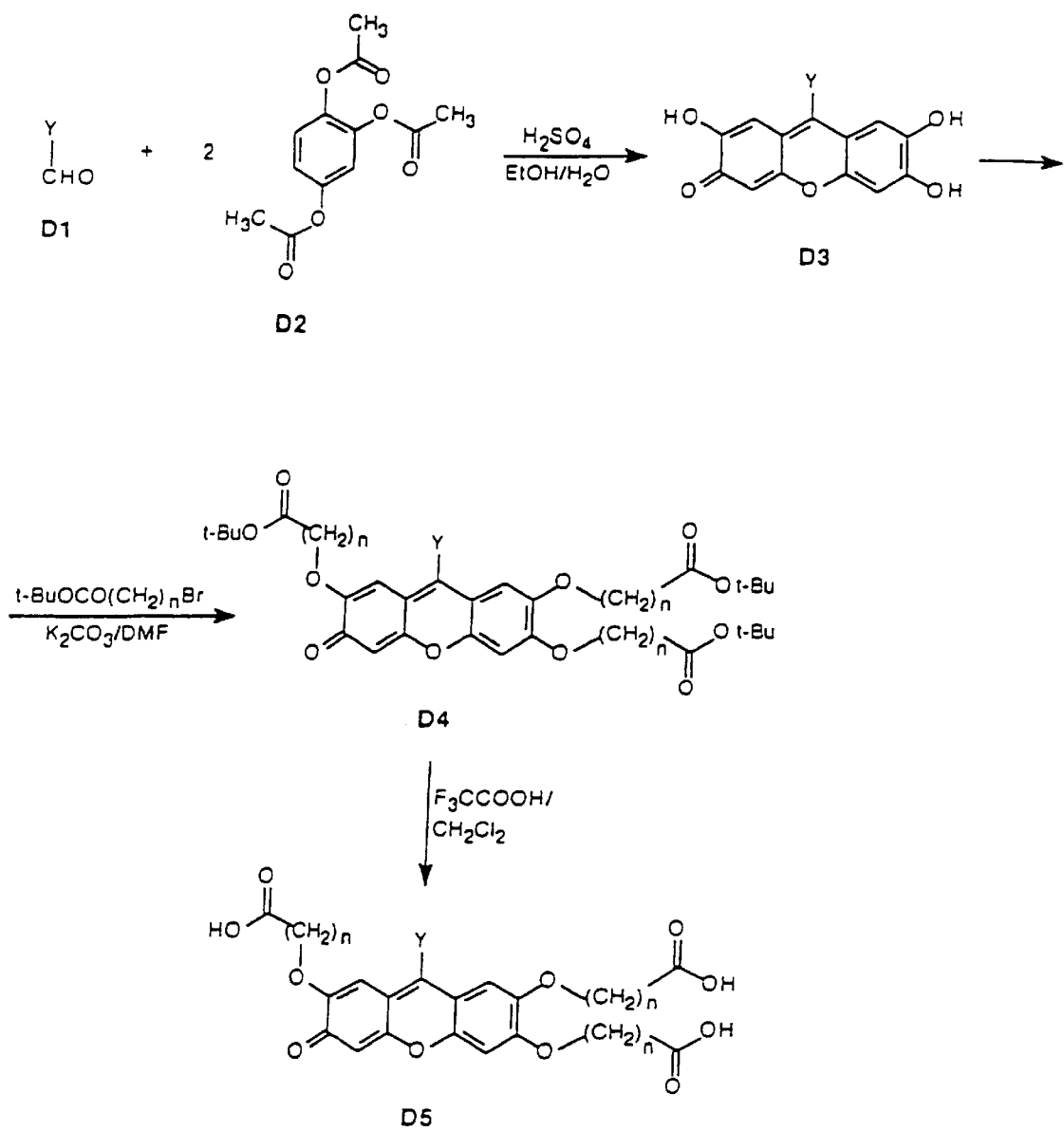
FIG. 3 is an illustration of a synthetic pathway of a luminophoric moiety which is a xanthenone group in accordance with the invention.

1.2 Preparation of the diaza-cryptands of the invention (FIGS. 2 and 3)

The preparation of the diaza-cryptands of the invention is exemplified in FIGS. 2 and 3 for two luminophoric moieties (aminonaphthalimide and xanthenone, respectively), wherein "Y" in each case represents an ionophoric moiety.
General Process of FIG. 2 (the Luminophoric Moiety is an Aminonaphthalimide Group)

Compounds of the invention having a single CH$_2$ group as a spacer between the luminophoric and the ionophoric moiety were prepared in that, first, the compound C 1, which may f.i. be the compound A13 (FIG. A), in which "Y" represents A12, was converted to the oxime C2 and by means of Zn in acetic acid was reduced to obtain the amine C3. Coupling to the luminophoric moiety in order to prepare the compound C9 of the invention is shown schematically in FIG. 2 by means of the aminonaphthalimide C8 prepared by reacting C6 with C7 in dimethylformamide in the presence of K$_2$CO$_3$.

Compounds of the invention having two CH$_2$ groups acting as a spacer between the luminophoric and the ionophoric moiety were prepared in that, first, the compound C1 was reacted to the compound C4 with a great excess of nitromethane in the presence of ammonium acetate, the compound C4 was subsequently reduced by means of LialH$_4$ in THF to obtain the amine C5. Coupling to the aminonaphthalimide C8 to prepare the compound C 10 is also shown schematically in FIG. 2.

Description of Individual Reaction Steps of FIG. 2

4-chloro-N-(4-carboxyphenylmethyl)-1,8-naphthalimide C8:

46.4 g (200 mmol) 4-chloro-1,8-naphthalenic acid anhydride C7, 30.2 g (200 mmol) 4-aminomethylbenzoic acid C6 and 13.8 g (100 mmol) $K_2CO_3$ were suspended in 2 l dimethylformamide, stirred at room temperature for 16 hours and at 60° C. for 6 hours. The mixture was subsequently poured into 4 l water and adjusted to pH 4 with 6 n HCl. The resulting precipitate was filtered off and dried at 60° C. for 18 min, wherein 36 g of off-white powder were obtained (yield: 51%).

Diaza-cryptand aldoxime C2 (o=1, p=1):

1 g (2.21 mmol) diaza-cryptand aldehyde A13 with o=1 and p=1 was suspended in 10 ml ethanol and 7 ml water. To this were subsequently added 0.31 g (4.42 mmol) hydroxylamine hydrochloride and 0.26 g (2.43 mmol) $Na_2CO_3$. The reaction mixture was warmed at 60° C. for 5 hours. After cooling, the solution was mixed with ice water. The oxime precipitated as an oil, was taken up in chloroform and washed with water. On drying and concentrating the organic solution, 0.83 g oxime were obtained as a light-brown oil (yield: 80%).

Diaza-cryptand amine C3 (o=1, p=1):

A solution of 0.83 g (1.77 mmol) diaza-cryptand aldoxime C2 with o=1 and p=1 in 12 ml acetic acid was prepared and 1.62 g (24.75 mmol) zinc added. The reaction mixture was stirred at room temperature overnight and subsequently at 65° C. for 3 hours. After cooling, the mixture was mixed with dichloromethane and filtrated to remove excess zinc and zinc salts. The precipitate was washed with dichloromethane. The filtrate was concentrated in vacuo, the yellow residue was subsequently mixed with water and adjusted to pH 9 with aqueous lithium hydroxide solution. The product was then extracted from the aqueous solution with dichloromethane and the solvent removed in vacuo. 0.56 g of dark yellow oil were obtained (yield: 70%).

4-(2-nitroethenyl)-diaza-cryptand C4 (o=1, p=1):

A solution of 1 g (2.21 mmol) diaza-cryptand aldehyde A13 with o=1 and p=1 in 4.5 ml acetic acid was prepared and stirred at room temperature for 10 min. Subsequently, 2.63 ml (2.97 g, 48.62 mmol) nitromethane were added and stirred at 60° C. for 5 hours. After cooling, the mixture was poured onto ice water, wherein there formed a dark red precipitate, which was exhausted and washed with water. On drying in an exsiccator, 0.6 g of product were obtained (yield: 55%).

4-(2-aminoethyl)-diaza-cryptand C5 (o=1, p=1):

In a three-necked flask provided with a nitrogen supply and a reflux cooler with calcium-chloride tubes, 0.46 g (12.1 mmol) $LiAlH_4$ were suspended in 25 ml dry tetrahydrofuran. Then, 0.6 g (1.21 mmol) 4-(2-nitroethenyl)-diaza-cryptand C4 with o=1 and p=1in 6 ml dry tetrahydrofuran were slowly added drop by drop. The mixture was subsequently stirred under reflux for 4 hours. The reaction mixture was cooled in an ice bath and excess $LiAlH_4$ was cautiously decomposed using a mixture of tetrahydrofuran and aqueous NaOH. The mixture was filtered, the precipitate washed with chloroform and the filtrate concentrated. The residue was taken up in chloroform, washed with water and the solution was concentrated, wherein 0.45 g of dark yellow oil were obtained (yield: 80%).

Diaza-cryptand fluoroionophore C9 (o=1 p=1):

0.56 g (1.23 mmol) diaza-cryptand amine C3 with o=1 and p=1, 0.42 g (1.23 mmol) 4-chloro-naphthalimide derivative C8 and 0.4 g (3.09 mmol) diisopropylethylamine were suspended in 2.5 ml N-methylpyrrolidinone. The reaction mixture was stirred for 24 hours at 60° C. under a nitrogen atmosphere. After cooling, the yellow solution was mixed with water, the product precipitating along with unreacted 4-chloro-naphthalimide derivative. The precipitate was filtrated, washed with water and dried in the exsiccator overnight. The mixture was then taken up in warm chloroform/methanol (3:1), filtrated, the solution was concentrated and the residue purified by means of column chromatography on silica gel and with chloroform/methanol (3:1) and 1% acetic acid as the mobile phase. 0.065 g of product (yield: 7%) were obtained.

Diaza-cryptand fluoroionophore C10 (o=1, p=1):

0.45 g (0.96 mmol) 4-(2-aminoethyl)-diaza-cryptand C5 with o=1 and p=1, 0.33 g (0.96 mmol) 4-chloro-naphthalimide derivative C8 and 0.31 g (2.4 mmol) diisopropylethylamine were suspended in 2.5 ml N-methylpyrrolidinone. The reaction mixture was stirred for 24 hours at 60° C. under a nitrogen atmosphere. After cooling, the yellow solution was mixed with water, the product precipitating along with unreacted 4-chloro-naphthalimide derivative. The precipitate was filtrated, washed with water and dried in the exsiccator overnight. The mixture was then taken up in warm chloroform/methanol (3:1), filtrated, the solution was concentrated and the residue purified by means of column chromatography on silica gel and with chloroform/methanol (3:1) and 1% acetic acid as the mobile phase. 0.074 g of product (yield: 10%) were obtained.

Process of FIG. 3 (the Luminophoric Moiety is a Xanthenone Group)

Diaza-cryptand-2,3,7-trihydroxyflurone D3 (o=1, p=1):

To a suspension of 1.67 g (6.63 mmol) 1,2,4-triacetoxybenzene D2 in 16 ml 50% ethanol, 1.4 ml concentrated sulfuric acid were added drop by drop, followed by 10 min of stirring and subsequent addition of 1.5 g (3.31 mmol) diaza-cryptand aldehyde D1 (=A13). The suspension was then stirred for 24 hours at 80° C. The mixture was subsequently mixed with water, adjusted to pH 5 with 25% tetramethylammonium hydroxide and allowed to stand overnight. The reaction mixture was decanted, the residue washed with water and subsequently mixed with methanol and stirred. On removing the solvent in vacuo, 0.67 g of red product were obtained (yield: 30%).

Diaza-cryptand-2,3,7-tri-t-butoxycarbonylmethoxyfluorone D4 (o=1, p=1):

0.67 g (1 mmol) diaza-cryptand-2,3,7-trihydroxyfluorone D3 with o=1 and p=1, 0.45 g (3 mmol) sodium iodide, 0.48 g (4.5 mmol) sodium carbonate and 0.88 g (4.5 mmol) t-butylbromoacetate were suspended in 5 ml dimethylformamide and stirred for 1 hour at 110° C. After cooling, the mixture was diluted with water and extracted with chloroform. The organic solution was washed with water, dried over sodium sulfate and concentrated. The crude product was then purified by means of column chromatography on silica gel using chloroform/methanol (9: 1), wherein 0.55 g of red viscous product were obtained (yield: 55%).

Diaza-cryptand-2,3,7-tri-carboxymethoxyfluorone D5 (o=1, p=1):

A solution of 0.55 g (0.54 mmol) diaza-cryptand-2,3,7-tri-t-butoxycarbonylmethoxyfluorone D4 with o=1 and p=1 in 2 ml dichloromethane was prepared. 0.25 ml trifluoroacetic acid were added and stirred for 4 hours at 40° C. The reaction mixture was then concentrated in vacuo and the residue dissolved in methanol. The solvent was partly evaporated and the procedure repeated twice in order to remove the trifluoroacetic acid as completely as possible. 0.36 g of red viscous product were obtained (yield: 90%).

2. Luminescence Properties of the Diaza-cryptands of the Invention

Figure 4:
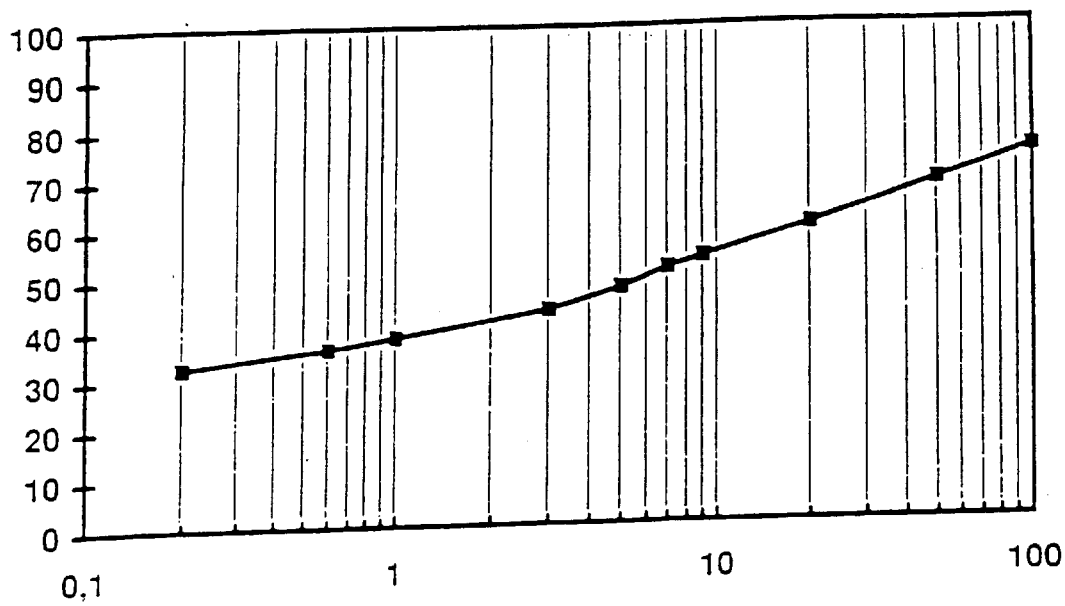
FIG. 4 is a graphical illustration of luminescence intensity for a diaza-cryptand fluoroionophore $C_9$ immobilized on cellulose versus concentration of alkali ions.
Figure 5:
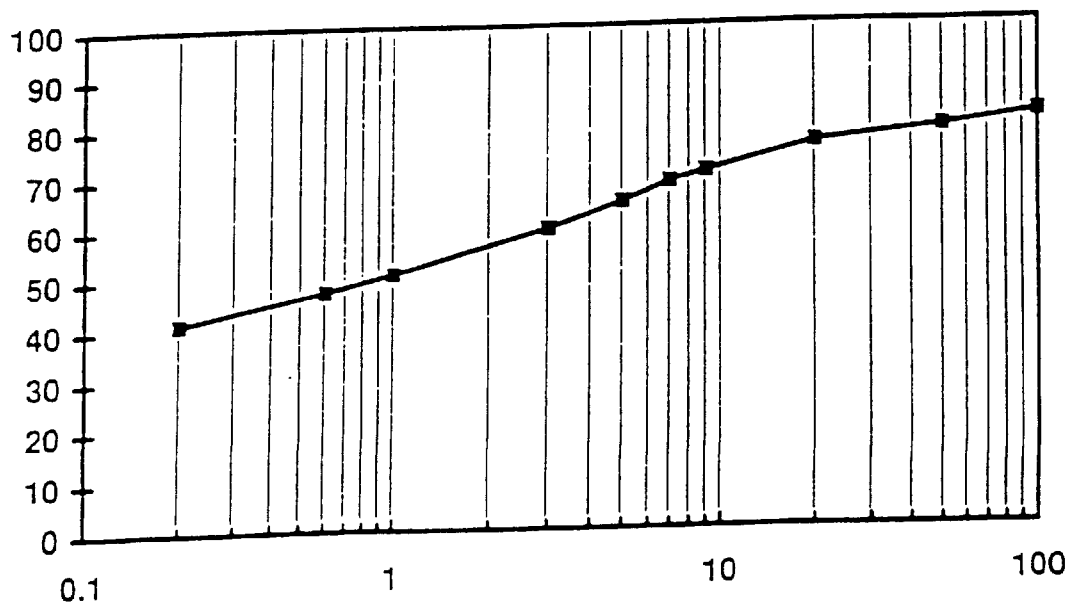
FIG. 5 is a graphical illustration of luminescence intensity for a diaza-cryptand fluoroionophore $C_{10}$ immobilized on cellulose versus concentration of alkali ions.
Figure 6:
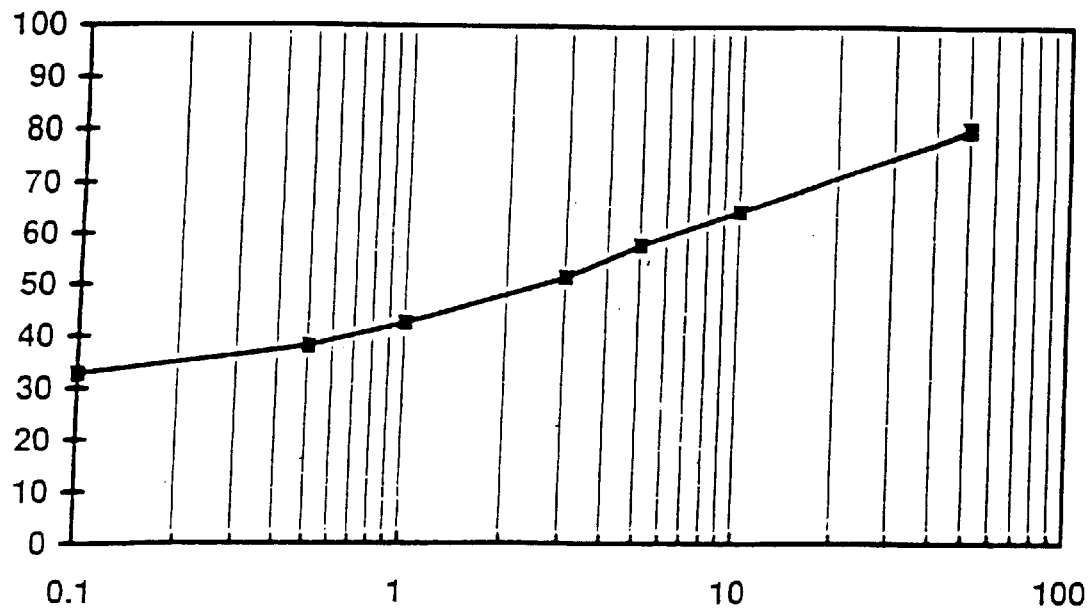
FIG. 6 is a graphical illustration of luminescence intensity for a diaza cryptand fluroionophore $D_5$ immobilized on cellulose versus concentration of alkali ions.

FIGS. 4, 5 and 6 show the luminescence properties of compounds of the invention immobilized on cellulose as a function of the given concentration of alkali ions. The ordinates of the represented diagrams indicate the respective relative luminescence intensities.

FIG. 4

FIG. 4 was obtained with the diaza-cryptand C9.
Immobilization on Cellulose Fibers (aminomodified) Was Done as Follows:

0.03 mmol of the diaza-cryptand C9, 0.06 g (0.3 mmol) N,N-dicyclohexyl-1,3-carboduimide, 0.4 g (0.3 mmol) N-hydroxysuccinimide and 5 g activated cellulose (prepared in accordance with SU-A-1,028,677, CA 99:177723h) were suspended in 2 ml dimethylformamide for 20 hours. The cellulose was then filtered off, washed 5 times with 5 ml dimethylformamide, 5 ml water, twice with 5 ml 0.2 n HCl, 5 ml water, twice with 5 ml 0.2 n NaOH, 10 times with 5 ml water, twice with 5 ml acetone and twice with 5 ml ether, and was dried for 16 hours at room temperature. Subsequently, the cellulose was sieved (25 $\mu$m).

Sensor Discs were Produced in the Following Manner:

0.25 g sieved (25 $\mu$m) aminocellulose fibers with immobilized crown ether C9 were suspended in 4.75 g 10% hydrogel D4 (Tyndale Plains-Hunter LTD. Ringoes, N. J. 08551) in 90% ethanol-water for 16 hours. The resulting homogenous dispersion was applied to a polyester foil (Melinex foil, ICI America) up to a dry density of 10 $\mu$m. This foil was coated over with 3% activated carbon in 10% D4 hydrogel up to a dry density of 5 $\mu$m, whereupon a small disc 2.5 cm in diameter was cut out. This disc was left in the buffer for at least 16 hours for activation.

A method of cutting and measuring sensor discs was described by M. J. P. Leiner and P. Hartmann in Sensors and Actuators B, 11 (1993), 281–189 ("Theory and Practice in optical pH sensing").

Figure 7:
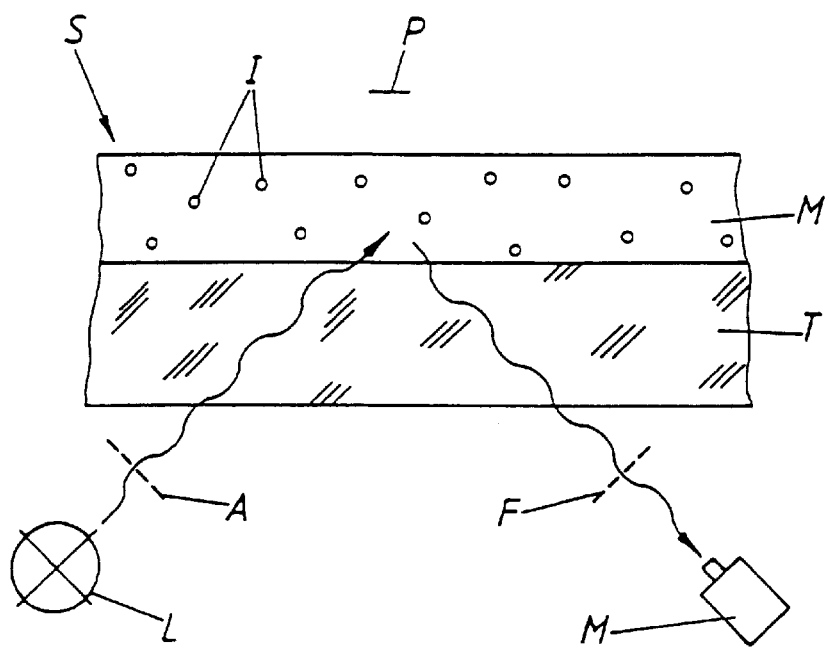
FIG. 7 is a schematic diagram of a sensor disc in accordance with the invention.

The sensor disc thus obtained was used in the measuring set-up represented schematically in FIG. 7.

In FIG. 7, the reference character S denotes a portion of the sensor disc. The compound immobilized on the cellulose fibers is denoted by I and is present in the hydrogel (layer M). This layer M is permeable to ions and is carried by a carrier T permeable to excitation and measuring radiation, which is a transparent foil.

According to the invention, the compound I can be bound to the ion-permeable matrix directly in a covalent manner or it can be present in the matrix in physically dissolved condition.

For measurement, the sensor disc was introduced into a thermostatted through-flow cell impervious to light and was contacted with samples P having different concentrations of sodium ions.

The optical measuring system consisted of a blue LED as the light source A, a photodiode M as the detector, optical filters A and F for selecting the wavelengths, a fiber-optic arrangement for conducting the excitation light into the polymer M and for conducting the emission light to the photodetector M as well as a device for electronic signal processing (not illustrated). At the excitation end there was utilized an interference filter (peak transmission at 480 nm) and at the emission end a 520 nm cut-off filter.

FIG. 4 shows the relative luminescence intensity (ordinate) as a function of different concentrations of potassium ions (0.2, 0.6, 1, 3, 5, 7, 9, 20, 50 and 100 mmol/l; abscissa; logarithmic scale), in each case in the presence of 145 mmol/l sodium ions. The measuring media was 30 mmol/l tris/HCl buffer, $CO_2$-free; pH: 7.4; 37° C.

FIG. 5

FIG. 5 was obtained in a manner analogous to FIG. 4, but with the diaza-cryptand C IO being used instead of the diaza-cryptand C9 and the luminescence intensity being measured depending on different concentrations of potassium ions (0.2, 0.6, 1, 3, 5, 7, 9, 20, 50 and 100 mmol/l; abscissa; logarithmic scale), in each case in the presence of 145 mmol/l sodium ions.

FIG. 7

FIG. 7 was obtained in a manner analogous to FIG. 4, but with the diaza-cryptand D5 being used instead of the diaza-cryptand C9 and the luminescence intensity being measured depending on different concentrations of potassium ions (0.1, 0.5, 1, 3, 5, 10 and 50 mmol/l; abscissa; logarithmic scale), in each case in the presence of 145 mmol/l sodium ions.

What is claimed is:

1. Method of determining the presence of an alkali ion in a sample comprising contacting the alkali ion with a compound having a luminophoric moiety and an ionophoric moiety wherein the compound is a diaza-cryptand of the general Formula I:

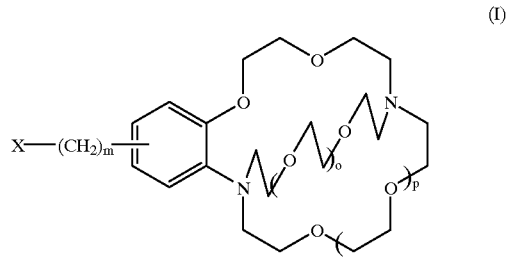

(I)

wherein m is 0, 1 or 2, o and p independently are 0, 1 or 2 and wherein X is the luminophoric moiety and is selected from the group consisting of an amino-naphthalimide group of the general Formula II:

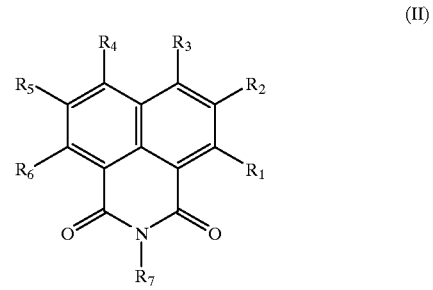

(II)

wherein one of $R_1$, $R_2$, $R_3$, $R_4$, $R_5$ and $R_6$ is an NH group through which X is bonded to the group —$(CH_2)-_m$ and the remainder and $R_7$ are independently selected from the group consisting of hydrogen, a lipophilic group, a hydrophilic group and a reactive group for coupling to a polymer and a xanthenone group of the general Formula III:

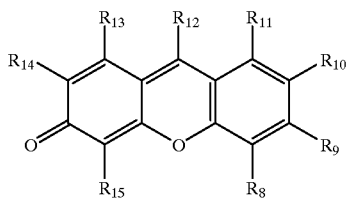

(III)

wherein m=0 and wherein one of $R_8$, $R_9$, $R_{10}$, $R_{11}$, $R_{12}$, $R_{13}$, $R_{14}$ and $R_{15}$ represents a chemical bond through which X is bonded directly to the ionophoric moiety and the remainder is selected from the group consisting of OH, $OR_{16}$ wherein $R_{16}$ is selected from the group consisting of a hydrophilic group and a lipophilic group, $OR_{17}$-G wherein $R_{17}$ is selected from the group consisting of a hydrophilic group and lipophilic group and G is a reactive group for coupling to a polymer, and —$(CH_2)_n$—COOH wherein n=0 to 17.

2. Method according to claim 1 wherein wherein o =0 and p =0.

3. Method according to claim 1 wherein o and p are different and are selected from the group consisting of 0 and 1.

4. Method according to claim 1 wherein o and p, are 1.

* * * * *

UNITED STATES PATENT AND TRADEMARK OFFICE
CERTIFICATE OF CORRECTION

PATENT NO. : 6,124,135
DATED : September 26, 2000
INVENTOR(S) : Leiner et al.

Page 1 of 3

It is certified that error appears in the above-identified patent and that said Letters Patent is hereby corrected as shown below:

Column 14,
Line 7, "wherein" (second occurrence) should be deleted
Line 12, "p," should read -- p --

Column 1,
Line 60- move all text to column 2, line 66

Column 2,
Line 18, move all text to column 2, line 66
Line 5, "$C_9$" should read -- C9 --
Line 8, "$C_{10}$" should read -- C10 --
Line 11, "diaza cryptand" should read -- diaza-cryptand --; "fluroionophore" should read -- fluoroionophore --; and "$D_5$" should read -- D5 --

Column 3,
Line 29, "f.i." (non-standard abbreviation) should read -- e.g., --
Line 34, "fi." should read -- e.g., --
Line 42, "1" should read -- 1 --.
Line 65, "R6" should read -- $R_6$ --

Column 4,
Line 30, "R4" should read -- $R_4$ --
Line 40, "f.i." should read -- e.g., --
Line 44, "f.i." should read -- e.g., --
Line 47, "f.i." should read -- e.g., --
Line 51, "f.i." should read -- e.g., --
Line 52, "f.i." should read -- e.g., --
Line 62, "f.i." should read -- e.g., --

Column 5,
Line 31, "FIG. 1" should read -- FIG. 1. --
Line 64, "o=1p=1," should read -- o=1, p=1,--

Column 6,
Line 29, "m, 1H)." should read -- (m, 1H). --
Line 59, "($CDCL_3$), should read -- ($CDCl_3$), --

UNITED STATES PATENT AND TRADEMARK OFFICE
CERTIFICATE OF CORRECTION

PATENT NO. : 6,124,135
DATED : September 26, 2000
INVENTOR(S) : Leiner et al.

It is certified that error appears in the above-identified patent and that said Letters Patent is hereby corrected as shown below:

Column 7,
Line 6, "(CDCL$_3$), should read -- (CDCl$_3$), --
Line 24, "(CDCL$_3$), should read -- (CDCl$_3$), --
Line 32, "tetrahyrofuran" should read -- tetrahydrofuran --
Line 43, "CDCL$_3$), should read -- (CDCl$_3$)," --

Column 8,
Line 53, "f.i." should read -- e.g., --
Line 67, "LialH$_4$" should read --LiAlH$_4$--.

Column 9,
Line 1, "C IO" should read -- C10 --
Line 65, "(0=1p=1):" should read -- (0=1, p=1): --

Column 10,
Line 33, "trihydroxyflurone" should read -- trihydroxyfluorone --

Column 11,
Line 1, "Done as Follows:" should read -- done as follows: --
Line 13, "Cellulose Fibers" should read -- cellulose fibers --; and "Was" should read -- was --

Column 12,
Line 3, "mmol/1" should read -- mmol/1 --
Line 8, C IO" should read -- C10 --

UNITED STATES PATENT AND TRADEMARK OFFICE
CERTIFICATE OF CORRECTION

PATENT NO. : 6,124,135
DATED : September 26, 2000
INVENTOR(S) : Leiner et al.

It is certified that error appears in the above-identified patent and that said Letters Patent is hereby corrected as shown below:

Column 12, cont'd,
Line 14, "FIG. 7" should read -- FIG. 6 --
Line 15, "FIG. 7" should read -- FIG. 6 --

Signed and Sealed this

Fifth Day of February, 2002

Attest:

JAMES E. ROGAN
*Director of the United States Patent and Trademark Office*

*Attesting Officer*